United States Patent
Tenniswood

[11] Patent Number: 6,146,136
[45] Date of Patent: *Nov. 14, 2000

[54] SELF-CLEANING DENTAL SUCTION DEVICE

[76] Inventor: James R. Tenniswood, 1008 8th Ave., Okeechobee, Fla. 34972

[*] Notice: This patent issued on a continued prosecution application filed under 37 CFR 1.53(d), and is subject to the twenty year patent term provisions of 35 U.S.C. 154(a)(2).

[21] Appl. No.: 09/267,282

[22] Filed: Mar. 12, 1999

[51] Int. Cl.[7] .................................................. A61C 17/06
[52] U.S. Cl. ............................................. 433/92; 604/319
[58] Field of Search ............................. 433/92; 604/319, 604/320, 35

[56] References Cited

U.S. PATENT DOCUMENTS

| | | | |
|---|---|---|---|
| 2,759,476 | 8/1956 | Henderson | 433/92 |
| 3,138,873 | 6/1964 | Bishop | 433/92 |
| 5,282,744 | 2/1994 | Meyer | 433/92 |
| 5,738,519 | 4/1998 | Tenniswood | 433/92 |

*Primary Examiner*—Gene Mancene
*Assistant Examiner*—Pedro Philogene

[57] ABSTRACT

Self-cleaning dental suction device comprising a collection tank having an inlet pipe oriented at a downward angle that intersects an interior wall of the tank in a manner to provide a self-cleaning swirling action of liquid waste and solid debris on the interior wall of the tank, a motor operably associated with the collection tank for generating a relative vacuum therein, and a drainage valve communicated to the collection tank for draining the contents of the collection tank. The tank vacuum is discontinued when the tank liquid level reaches a maximum level by a float valve closing off communication between the motor and the collection tank or when the vacuum motor is de-energized.

7 Claims, 3 Drawing Sheets

6,146,136

SELF-CLEANING DENTAL SUCTION DEVICE

FIELD OF THE INVENTION

The present invention relates to dental suction or evacuator devices for evacuating saliva, water, tooth chips, and other fluid entrained debris from the mouth of a dental patient.

BACKGROUND OF THE INVENTION

Modern dental care facilities include one or more work stations or operatories where dental procedures are performed on the patient and where a suction or evacuator device is provided to remove water, tooth chips, and other fluid entrained debris from the patient's mouth during the procedure. For example, during drilling and filling of tooth cavities, tooth chips and debris are generated in the patient's mouth. Water typically is sprayed on the tooth being repaired to facilitate the procedure. The water and tooth chips and debris entrained in the water are removed during the procedure by an aspirator tip placed in the mouth and connected to a central suction or evacuator device that may service all of the operatories. The suction device typically comprises a suction fan or blower associated with a central collection tank of limited capacity (e.g. 5 gallons or less) into which the water, tooth chips, and other debris are drawn and collected.

Many commercially available suction devices require regular cleaning and maintenance. Liquid waste evacuated from the patient's mouth enters the inlet pipe and is released from the inlet pipe to the holding tank which causes the liquid waste with entrained solid debris to splatter and adhere onto the sides of the tanks such that dismantling and cleaning of the tank is required to remove the adhered tank wall waste. Methods intended to alleviate the problem of debris adherence include filtration or collection in a reservoir, but these methods still require regular cleaning and maintenance of the tank as liquid waste remains on the walls.

Other disadvantages of prior dental suction devices include inadequate drainage of the collection tank, possible overheating of the motor, and bothersome motor location.

An object of the present invention is to provide an improved dental suction device that overcomes these disadvantages of commercially marketed dental wet/dry suction devices and provides a suction device that includes a self-cleaning collection tank.

SUMMARY OF THE INVENTION

The present invention provides an improved self-cleaning wet/dry dental suction device comprising a collection tank adapted to be communicated to one or more aspirator tips and having an inlet pipe oriented at a downward angle that intersects an interior wall of the tank in a manner to provide a self-cleaning swirling action of liquid waste and solid debris on the interior wall of the tank. A vacuum generating electric motor is operably associated with the collection tank for generating a vacuum (sub-ambient pressure) therein. A drainage valve is communicated to the collection tank for draining the contents of the collection tank. The tank vacuum is discontinued when the tank liquid level reaches a maximum level by a float valve closing off communication between the motor and the tank.

In one embodiment of the invention, the collection tank comprises a one-piece fiberglass reinforced plastic lower upright tank supported on a fiberglass reinforced plastic base and a fiberglass reinforced plastic removable cover vacuum tight sealed on top of the lower tank. Preferably the inlet pipe to the collection tank includes a lateral tubular section, an ascending tubular section, and a descending tubular section oriented at a downward angle that intersects the interior wall of the collection tank to provide the self-cleaning swirling action of liquid waste and solid debris. The inlet pipe enters the collection tank at an intermediate location along its vertical axis to this end. A vacuum is produced in the collection tank via a suction pipe that extends upwardly from the base and includes an inverted bend section within the cover. A float valve is disposed at a lower end of the bend section to define a maximum fluid level in the tank whereby the float valve closes off the vacuum if liquid level in the tank reaches the maximum level. At this liquid level in the tank, ambient pressure is provided in the tank and a drainage swing check valve near the bottom of the tank automatically opens from weight of the liquid debris to drain the tank. A pressure relief valve is provided to supply ambient air to the vacuum-generating motor to cool it when the float valve closes off the suction pipe. The float valve returns to an open position when ambient pressure is provided in the tank.

The above and other objects of the invention will become more readily apparent from the following detailed description and the following drawings.

DETAILED DESCRIPTION OF THE INVENTION

The present invention provides a self-cleaning, improved wet/dry dental suction device for servicing one or more work stations or operatories where dental procedures are performed on patient(s) and where a suction or evacuator device is needed to remove water, tooth chips, and other fluid entrained debris from the patients' mouths during various procedures that may be performed.

Figure 1:
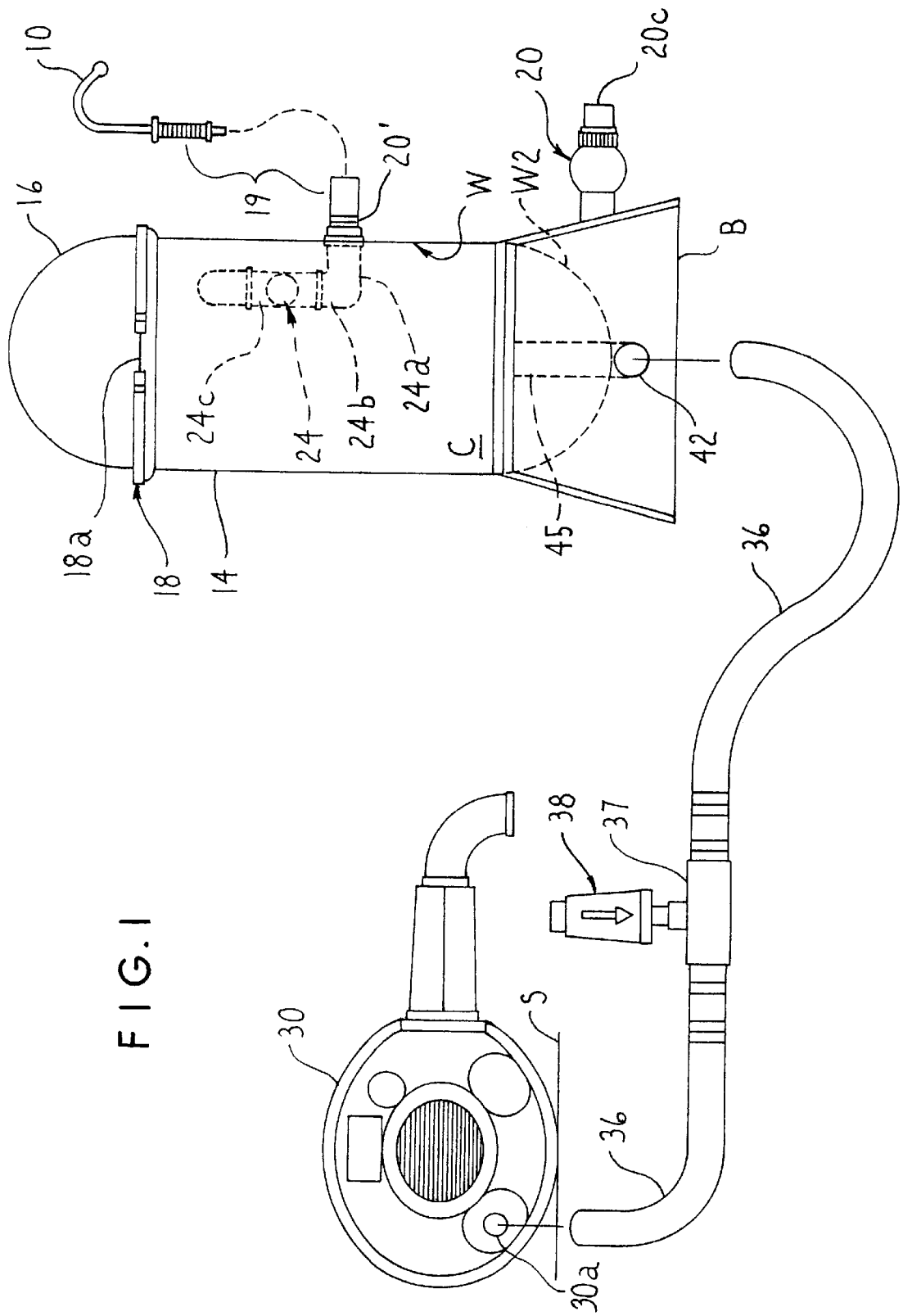
FIG. 1 is an elevational view of a dental suction device pursuant to an embodiment of the present invention with an aspirator tip and vacuum-generating motor shown in communication with a collection tank.
Figure 2:
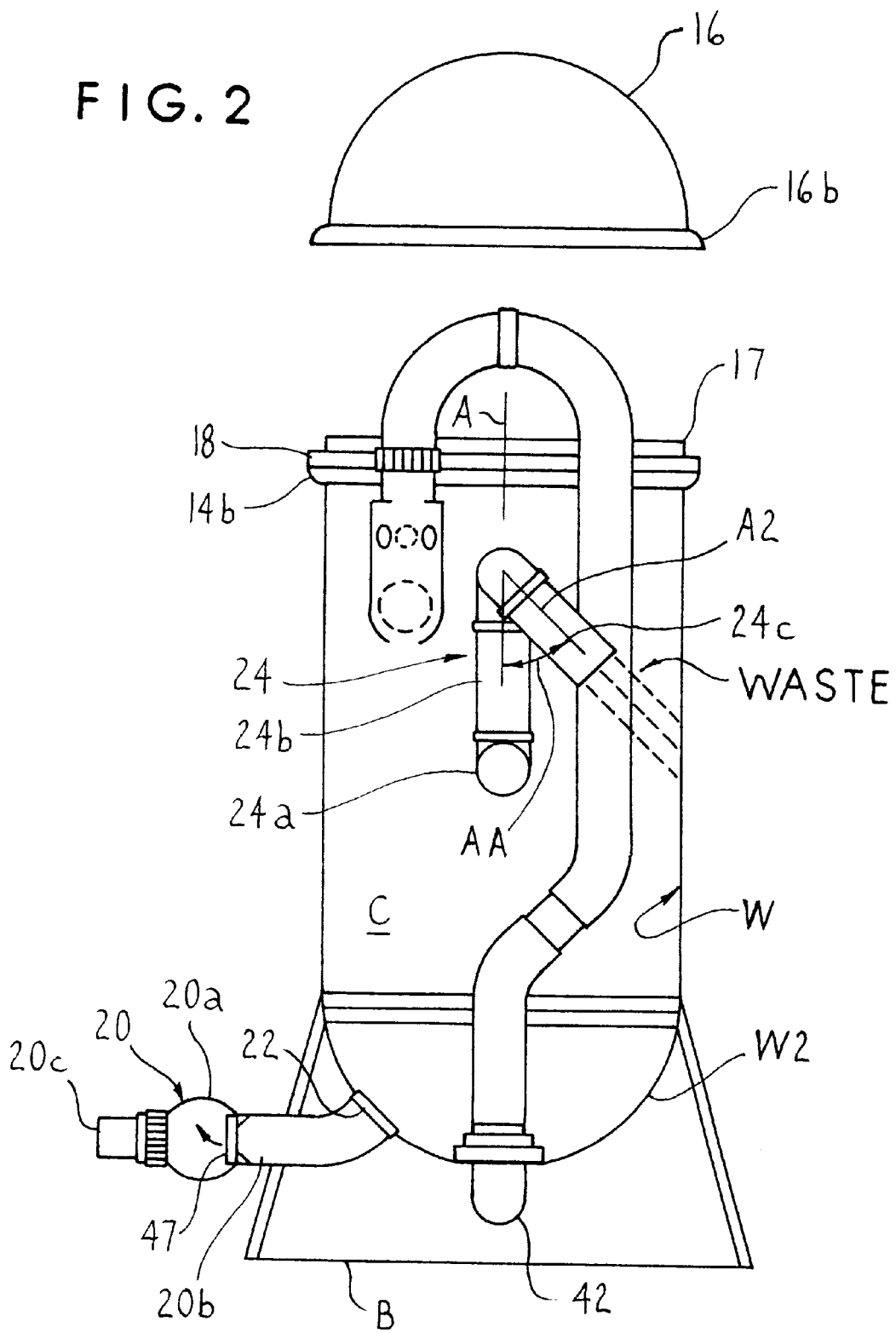
FIG. 2 is an exploded view of a collection tank with tank side wall removed to show the inlet and suction pipe assembled in accordance with an embodiment of the present invention.
Figure 3:
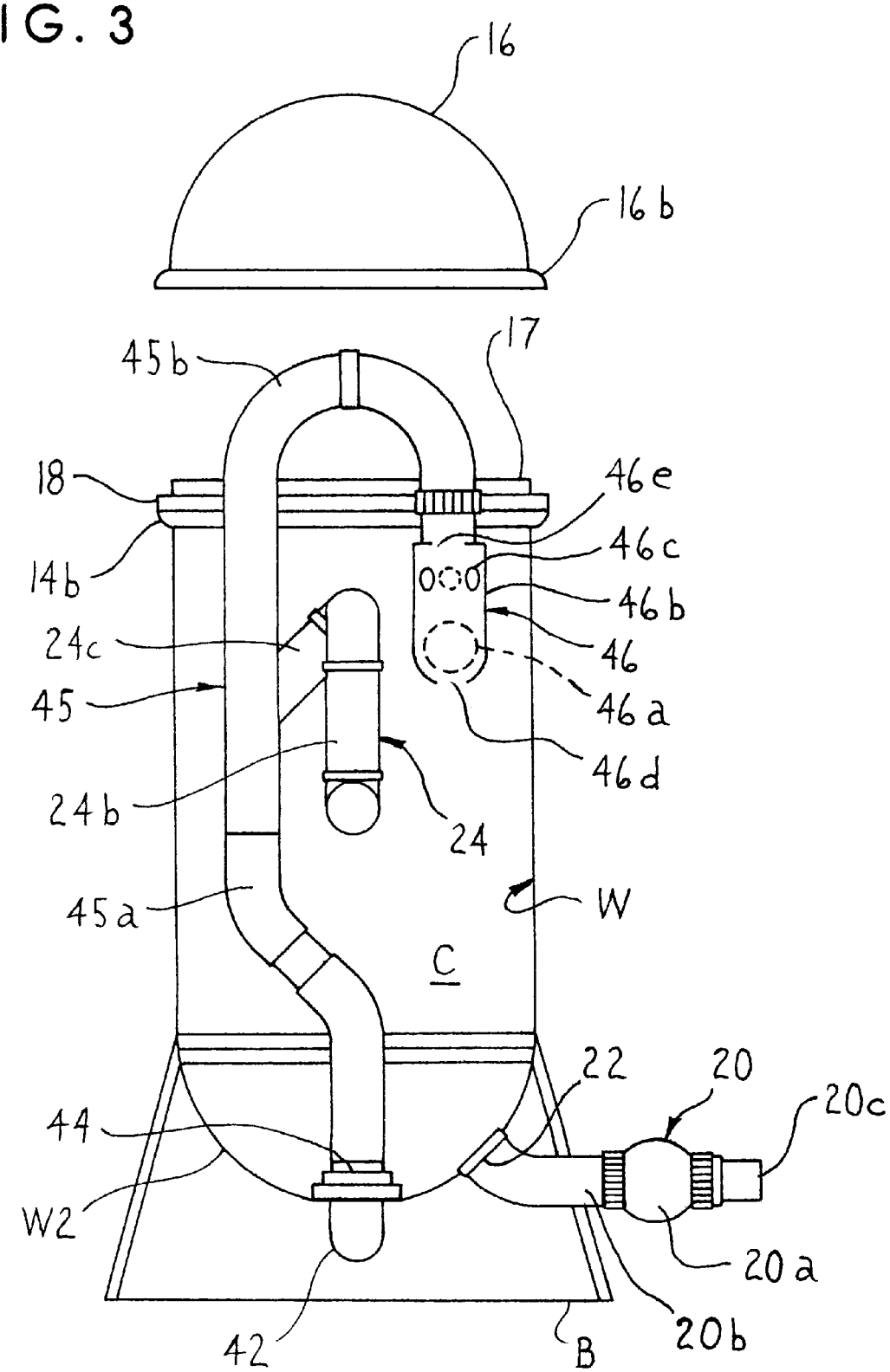
FIG. 3 is a exploded view of a collection tank taken 180° from FIG. 2.

Referring to FIGS. 1–3, a self-cleaning dental suction device in accordance with an embodiment of the invention is shown for purposes of illustration. The self-cleaning dental suction device is adapted for use with one or more conventional aspirator tips 10 (one shown) for positioning in a patient's mouth at respective operatories. The aspirator tips 10 form no part of the invention, however. Each aspirator tip 10 is communicated to the inlet pipe 24 of a collection tank 14 by a flexible conduit 19 (one shown). The conduit 19 is connected by conventional PVC compression fitting 20' (2 inch inner diameter), to the collection tank 14 located about 16 inches above the bottom of the base B, so as to communicate the aspirator tips 10 to the inlet pipe 24.

The collection tank 14 comprises a fiberglass reinforced lower upright cylindrical tank having upright wall W and a bottom concave wall W2 molded as a one-piece tank. The tank 14 is supported on base B and fastened thereto by a suction pipe assembly to be described below. The tank also includes a removable domed shroud or cover 16, made of a fiberglass reinforced plastic. The cover 16 is vacuum tight sealed to the upper edge of the collection tank 14 with a conventional stainless steel sealing band 18 and annular rubber gasket 17 (½ inch diameter) placed between the lip 14b of the tank 14 and lip 16b of cover 16. The band 18 includes a threaded rod 18a to draw the band tightly about circumferential lips 14b, 16b of the collection tank 14 and cover 16. The entire assembly of the collection tank 14 and cover 16 is preferably 34 inches in length from base B to cover 16 and 12 inches outer diameter.

The interior chamber C of the collection tank 14 communicates to the plastic (e.g. PVC) inlet pipe 24 of a given diameter (e.g. 2 inch inner diameter). Inlet pipe 24 includes a lateral (e.g. horizontal) tubular section 24a, an ascending tubular section 24b, and a descending tubular section 24c that is oriented for swirling liquid and solid debris onto the wall W of the interior chamber C of the collection tank 14. The inlet pipe 24 is made of conventional PVC pipe sections and fittings welded together by conventional PVC adhesive. The ascending tubular section 24b is communicated to the descending tubular section 24c and provides a vertical rise needed for proper positioning of the descending section 24c to produce the self-cleaning action of evacuated liquid and solid waste. The descending tubular section 24c is communicated to the ascending tubular section 24b and the interior chamber C of the collection tank 14 for discharging waste received from the aspirator tip 10 in a self-cleaning swirling action that intersects wall W. The longitudinal centerline axis A2 of descending section 24c is oriented at an acute angle AA relative to the vertical longitudinal axis A of the collection tank 14 between 30° and 70°, preferably 45° to this end. The descending section 24c is located in a vertical plane that is parallel to a diametral plane of the tank 14 (i.e. a plane containing a diameter of the tank).

When a relative vacuum is provided in the interior chamber C of the collection tank 14 by vacuum-generating electric motor 30, liquid waste and solid debris are ejected out of the descending tubular section 24c onto the interior wall W of the collection tank 14 at an angle that intersects wall W and produces a self-cleaning, swirling motion of liquid and solid debris around the interior wall W of the collection tank 14.

The remote vacuum generating motor 30 is communicated by a flexible vacuum line 36 to the collection tank 14 for generating a sub-ambient pressure therein. The vacuum generating motor 30 is effective to generate a relative vacuum in the interior chamber C of the collection tank 14 and thus at aspirator tip(s) 10. To this end, the vacuum-generating motor 30 can comprise a 3 horsepower electric motor blower available as model 2BH1 410 1HB 48Z from Siemens. The motor 30 can be located on a suitable support S at a remote location from tank 14. The hose 36 typically has a length of about 4 to 6 feet to permit placement of motor 30 at a convenient location.

The reinforced flexible vacuum line 36 (2 inches inner diameter) is connected to the vacuum-generating motor 30 and to the collection tank 14. The line 36 includes a conventional pressure relief valve 38 that automatically opens when additional cooling is required by the vacuum-generating motor 30 as a result of float valve 46 closing off communication between the motor 30 and the tank 14, as described below. The reinforced flexible line connects at one end to the intake port 30a of the motor 30 and connects at the opposite end to an elbow type fitting 42 at the bottom of base B of the collection tank 14.

The pressure relief valve 38 is connected to the flexible vacuum line 36 by a PVC "T" fitting 37 (2 inch by 1¼ inch)
and may be located at a position along the flexible vacuum line 36 that provides sufficient air to cool the vacuum-generating motor 30. A pressure relief valve 38 of the type described is commercially available as model 2BX 2114-Z 280 Mbar from Siemens.

A suction pipe 45 communicates the elbow fitting 42 to the interior chamber C of the collection tank 14 for evacuating the collection tank 14. Fitting 42 is sealed in the wall W2 by a PVC coupling 44 (male and female coupling with adhesive, 2 inch inner diameter). The suction pipe 45 is made of a plastic (e.g. PVC) of a given diameter (2 inch inner diameter). The suction pipe includes an upright pipe section 45a, an inverted bend section 45b, and a float valve 46 as shown best in FIG. 3. The upright pipe section 45a is connected to the fitting 42 and extends upward through converging bottom wall W2 with a PVC coupling 44 to seal and fully support the suction pipe within of the interior chamber C of the collection tank 14. The upright pipe section 45a comprises conventional PVC pipes and fittings welded together. The suction pipe 45 includes an uppermost inverted 180° bend section 45b enclosed in the cover 16 collection tank 14. The inverted bend section 45b communicates the vertical pipe 45a to the float valve 46 located at the lower end of the bend section 45b. The float valve 46 includes plastic (e.g. PVC) cylindrical housing 46b having an inner diameter of 2½ inches and an outer length of 7 inches, and containing a rubber ball float 46a ( inches diameter). The housing 46b includes a bottom circular opening 46d, 5/16 inch in diameter. The housing 46b includes multiple circular air intake ports 46c; for example 3 intake ports separated 120° apart and 1½ inch diameter, and a valve seat 46e with 1½ inch diameter opening. The rubber float 46a floats on the liquid waste in the interior chamber C of the collection tank 14 and rises as the liquid waste level rises. At a maximum liquid waste level (e.g. 9 gallons), the rubber float 46a seals the valve seat 46e to stop communication between suction pipe 45 and chamber C. Discontinuance of the vacuum in chamber C in this manner prevents overfilling of the chamber C with liquid/ solid waste.

A drain valve 20 is communicated to the collection chamber C at wall W2 for draining its contents when the vacuum-generating motor 30 is de-energized typically at the end of the work day for example or when float valve 46 shuts off suction pipe 45 from chamber C. The motor 30 is de-energized by an appropriate manual switch or by unplugging the motor. When motor 30 is shut off, ambient pressure is provided by reverse airflow to the tank 14 via hose 36. When the float valve 46 seals off suction pipe 45, ambient pressure is provided in tank 14 by reverse airflow to tank 14 from the aspirator tip(s) 10. In either event, the drain valve 20 opens under weight of liquid/ solid debris in collection tank 14 to drain the debris. After the tank 14 is drained, the vacuum-generating motor 30 can be re-energized for further operation of the dental suction device.

As shown best in FIG. 2, the drain valve 20 comprises a plastic (e.g. PVC) central housing 20a having a first pipe section 20b of given diameter (e.g. 1½ inch inner diameter) at one end connected to the collection tank 14 by a conventional PVC compression fitting 22 (1½ inch inner diameter) or other means disposed on the tank wall and a second pipe section 20c of similar diameter at the opposite end communicated to a sanitary sewer drain pipe. The drain valve housing 20a has an enlarged cross section (1½ inch) to permit discharge of large solid particles. A drain valve of the type described is commercially available as Series 1520-20 PVC swing check valve shown as 47 (1½ inch diameter) from Flo Control, Inc., subsidiary of Bufftton Corp. 3210 Winona Ave., Burbank, Calif.

The dental suction device of the present invention is advantageous as a result of its self-cleaning action as compared to the commercially available suction devices requiring daily cleaning and maintenance. Moreover, the dental suction device includes an enlarged drain valve, overheating protection for the vacuum-generating motor, and the ability to place the motor in a convenient location.

Although the invention has been described in terms of specific embodiments thereof, it is understood that modifications and changes can be made thereto within the scope of the invention and appended claims.

I claim:

1. A dental suction device comprising a collection tank having a tank inlet communicated to an aspirator and oriented at a downward angle that intersects an interior side wall of the tank in a manner to provide a self-cleaning swirling action of fluid and solid debris entering said tank, a vacuum-generating motor operably associated with said collection tank for generating a relative vacuum therein, and a drainage valve disposed proximate a bottom of the collection tank for draining the fluid and solid debris.

2. The device of claim 1 wherein said collection tank comprises a fiberglass reinforced plastic upright lower tank on a base and a one-piece fiberglass reinforced plastic removable cover vacuum tight sealed to said lower tank.

3. The device of claim 2 wherein said vacuum-generating motor is connected to a suction pipe extending upward from the bottom of said collection tank, said suction pipe having an inverted bend section within said cover and including a float valve disposed at a lower end of said bend section, said float valve being operable to close off said tank from said motor when liquid waste in the tank reaches a maximum level.

4. The device of claim 2 wherein said tank inlet comprises a lateral tubular section, an ascending tubular section, and a descending tubular discharge section oriented at an angle downwardly relative to a vertical axis of the collection tank to provide the self-cleaning swirling action of liquid waste and solid debris.

5. The device of claim 2 wherein said vacuum motor is remote from said tank and connected thereto by a flexible vacuum line, said vacuum line having a pressure relief valve.

6. The device of claim 5 wherein said vacuum line is communicated to a fitting at a lowermost bottom of said tank base.

7. The device of claim 3 including a valve operable when the float valve closes off said tank from said motor to provide an airflow to said motor.

* * * * *